US010750961B2

(12) United States Patent
Kuwabara (10) Patent No.: US 10,750,961 B2
(45) Date of Patent: Aug. 25, 2020

(54) DIAGNOSIS ASSISTANCE APPARATUS, DIAGNOSIS ASSISTANCE METHOD, DIAGNOSIS ASSISTANCE PROGRAM

(71) Applicant: OMRON HEALTHCARE Co., Ltd., Muko-shi, Kyoto (JP)

(72) Inventor: Mitsuo Kuwabara, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 251 days.

(21) Appl. No.: 15/974,831

(22) Filed: May 9, 2018

(65) Prior Publication Data

US 2018/0256050 A1   Sep. 13, 2018

Related U.S. Application Data

(63) Continuation of application No. PCT/JP2016/082339, filed on Oct. 31, 2016.

(30) Foreign Application Priority Data

Nov. 10, 2015  (JP) ................................. 2015-220588

(51) Int. Cl.
*A61B 5/00* (2006.01)
*A61B 5/024* (2006.01)
(Continued)

(52) U.S. Cl.
CPC ............ *A61B 5/02438* (2013.01); *A61B 5/00* (2013.01); *A61B 5/0002* (2013.01); *A61B 5/021* (2013.01);
(Continued)

(58) Field of Classification Search
CPC ... A61B 5/02438; A61B 5/742; A61B 5/0002; A61B 5/022; A61B 5/00; A61B 5/02;
(Continued)

(56) References Cited

U.S. PATENT DOCUMENTS

2006/0200011 A1 *  9/2006  Suzuki ................. A61B 5/0205
                                                                      600/301
2009/0063098 A1 *  3/2009  Chang ..................... G16H 40/63
                                                                      702/187

FOREIGN PATENT DOCUMENTS

JP       2000-152918 A    6/2000
JP       2006-212218 A    8/2006
(Continued)

OTHER PUBLICATIONS

Jan. 24, 2017 International Search Report issued in International Patent Application PCT/JP2016/082339.

*Primary Examiner* — Scott M. Getzow
(74) *Attorney, Agent, or Firm* — Oliff PLC (57) ABSTRACT

Provided are diagnosis assistance apparatus, diagnosis assistance method, and diagnosis assistance program, according to which it is possible to effectively assist diagnosis by making it easy to understand a state of biological information of a measurement subject. A diagnosis assistance apparatus includes: biological information analysis unit configured to analyze a plurality of pieces of biological information that are measured from a measurement subject and are stored along with measurement times in a storage medium, and calculate an occurrence frequency of a fluctuating state in which the biological information fluctuates by a threshold or more in a predetermined period and representative value for fluctuation amount of the biological information in the fluctuating state that occurs in the predetermined period; and an analysis result output unit configured to output a graph indicating an analysis result obtained by associating occurrence frequency and representative value that were calculated by the biological information analysis unit.

8 Claims, 6 Drawing Sheets

(51) Int. Cl.
 *A61B 5/021* (2006.01)
 *A61B 5/022* (2006.01)
 *G16H 15/00* (2018.01)
 *G16H 50/20* (2018.01)
(52) U.S. Cl.
 CPC .............. *A61B 5/022* (2013.01); *A61B 5/742* (2013.01); *G16H 15/00* (2018.01); *G16H 50/20* (2018.01)
(58) Field of Classification Search
 CPC ...... A61B 5/021–02133; A61B 5/7275; A61B 5/746; G16H 50/20; G16H 15/00
 See application file for complete search history.

(56)  References Cited

FOREIGN PATENT DOCUMENTS

| | | |
|---|---|---|
| JP | 2008-206920 A | 9/2008 |
| JP | 2013-183974 A | 9/2013 |

\* cited by examiner

DIAGNOSIS ASSISTANCE APPARATUS, DIAGNOSIS ASSISTANCE METHOD, DIAGNOSIS ASSISTANCE PROGRAM

TECHNICAL FIELD

The present invention relates to a diagnosis assistance apparatus, diagnosis assistance method, and a diagnosis assistance program.

BACKGROUND ART

Biological information such as blood pressure values, a pulse rate, and a heart rate of a body normally changes relatively significantly in the course of day. Also, these pieces of biological information are pieces of biological information that fluctuate significantly due to diseases such as sleep apnea syndrome and heart disease. For this reason, in order to perform diagnosis or the like, a biological information measurement apparatus is attached to a measurement subject, and biological information is measured and recorded continuously (e.g., in intervals of several hours or every heartbeat).

Patent Document 1 discloses a system for continuously measuring blood pressure values, in which alarm information is created and recorded when blood pressure values fall below a predetermined value, and the daily number of occurrences of the alarm information in, for example, a ten-day period, is graphed and output.

CITATION LIST

Patent Literature

Patent Document 1: JP 2008-206920A

SUMMARY OF INVENTION

Technical Problem

In diagnosis performed using biological information such as the blood pressure values, it is important to determine the risk of a disease such as a cardiovascular event based not only on whether or not there is fluctuation in the biological information, but also on the amount of fluctuation in the biological information. However, as shown in Patent Document 1, if only the number of instances that a blood pressure drop occurred is graphed and output, it is insufficient for assisting diagnosis.

The present invention was made in view of the above-described circumstances and aims to provide a diagnosis assistance apparatus, a diagnosis assistance method, and a diagnosis assistance program, according to which it is possible to effectively assist diagnosis by making it possible to easily understand a state of biological information of a measurement subject.

Solution to the Problem

A diagnosis assistance apparatus of the present invention includes: a biological information analysis unit configured to analyze a plurality of pieces of biological information that are measured from a measurement subject and are stored along with measurement times in a storage unit, and calculate an occurrence frequency of a fluctuating state in which the biological information fluctuates by a threshold or more in a predetermined period and a representative value for information indicating fluctuation content of the biological information in the fluctuating state that occurs in the predetermined period; and an analysis result output unit configured to output information indicating an analysis result obtained by associating the occurrence frequency and the representative value that were calculated by the biological information analysis unit.

A diagnosis assistance method of the present invention includes: a biological information analysis step of analyzing a plurality of pieces of biological information that are measured from a measurement subject and are stored along with measurement times in a storage unit, and calculating an occurrence frequency of a fluctuating state in which the biological information fluctuates by a threshold or more in a predetermined period and a representative value for information indicating fluctuation content of the biological information in the fluctuating state that occurs in the predetermined period; and an analysis result output step of outputting information indicating an analysis result obtained by associating the occurrence frequency and the representative value that were calculated in the biological information analysis step.

A diagnosis assistance program of the present invention is for causing a computer to execute: a biological information analysis step of analyzing a plurality of pieces of biological information that are measured from a measurement subject and are stored along with measurement times in a storage unit, and calculating an occurrence frequency of a fluctuating state in which the biological information fluctuates by a threshold or more in a predetermined period and a representative value for information indicating fluctuation content of the biological information in the fluctuating state that occurs in the predetermined period; and an analysis result output step of outputting information indicating an analysis result obtained by associating the occurrence frequency and the representative value that were calculated in the biological information analysis step.

Advantageous Effects of the Invention

According to the present invention, it is possible to provide a diagnosis assistance apparatus, a diagnosis assistance method, and a diagnosis assistance program, according to which it is possible to effectively assist diagnosis by making it possible to easily understand a state of biological information of a measurement subject.

DESCRIPTION OF EMBODIMENTS

Hereinafter, an embodiment of the present invention will be described with reference to the drawings.

Figure 1:
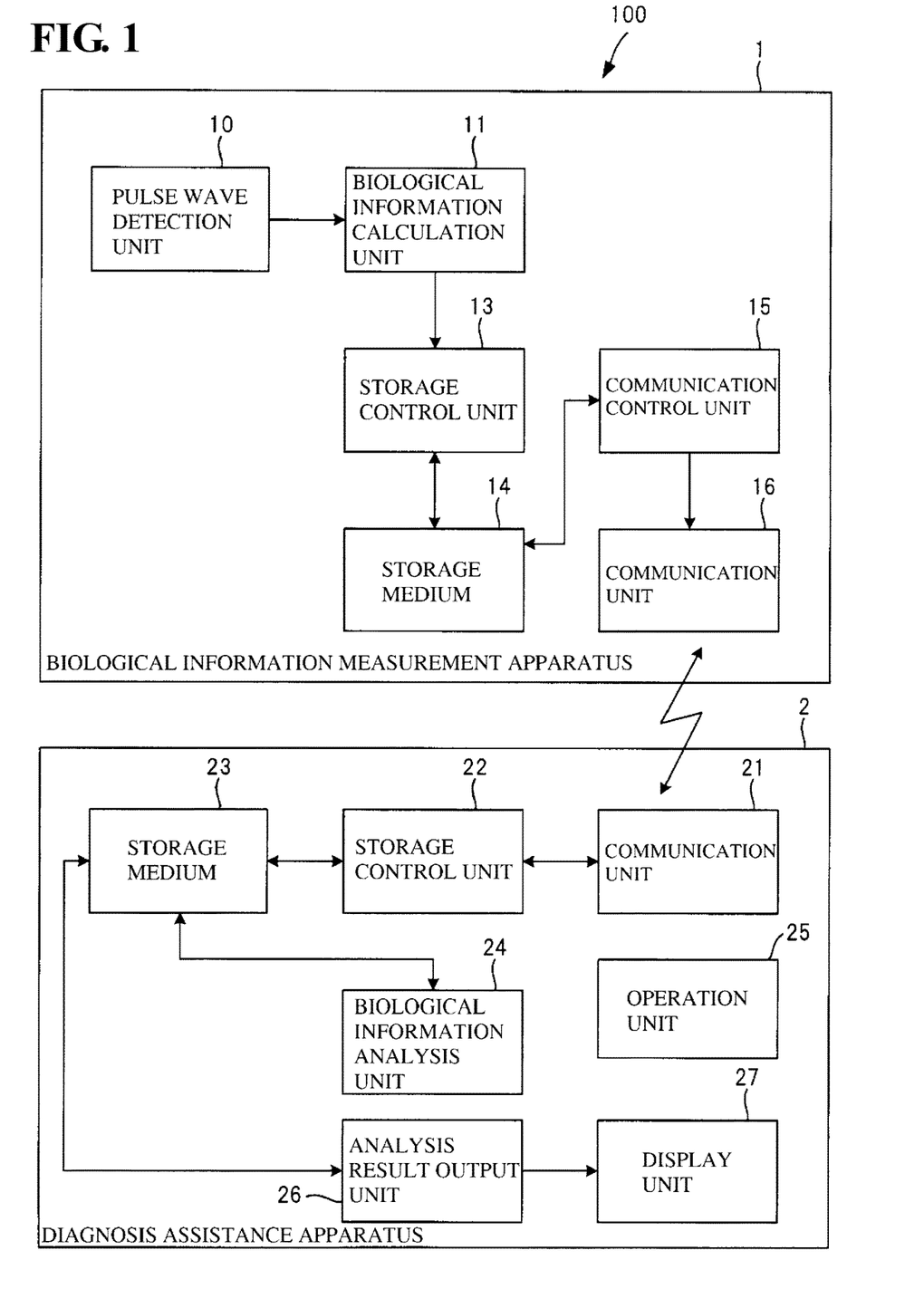
FIG. 1 is a diagram showing a schematic configuration of a diagnosis assistance system 100 for illustrating an embodiment of the present invention.

FIG. 1 is a diagram showing a schematic configuration of a diagnosis assistance system 100 for illustrating an embodiment of the present invention. The diagnosis assistance system 100 includes a biological information measurement apparatus 1 and a diagnosis assistance apparatus 2.

The biological information measurement apparatus 1 is portable and is used while worn on the wrist of a measurement subject serving as a living body.

The biological information measurement apparatus 1 includes a pulse wave detection unit 10, a biological information calculation unit 11, a recording control unit 13, a storage medium 14 such as a flash memory, a ROM (Read Only Memory) or a memory card, a communication control unit 15, and a communication unit 16. The storage medium 14 may be detachable from the apparatus.

The biological information calculation unit 11, the recording control unit 13, and the communication control unit 15 are functional blocks that are constituted by a processor executing a program.

The pulse wave detection unit 10 detects a pulse wave from the wrist of the measurement subject in a non-invasive manner.

A pulse wave detection unit 10 that detects a pressure pulse wave serving as a pulse wave through tonometry, for example, is used as the pulse wave detection unit 10. The pulse wave detection unit 10 may detect a volume pulse wave as the pulse wave. The pulse wave detection unit 10 may detect a pulse wave with reflected light from an artery, obtained by emitting light to the artery.

The pulse wave detection unit 10 detects a pulse wave generated for each heartbeat (a period in which the heart beats once) and transmits the detected pulse wave to the biological information calculation unit 11.

Based on the pulse wave detected by the pulse wave detection unit 10, the biological information calculation unit 11 calculates blood pressure information serving as the biological information for each heartbeat or for every multiple heartbeats (a frequency of once for multiple heartbeats). In the present description, the time at which the pulse wave used to calculate the blood pressure information is detected is defined as the time at which the blood pressure information is measured.

The blood pressure information includes at least one of the systolic blood pressure (SBP), the diastolic blood pressure (DBP), and the mean blood pressure (MBP).

A known method can be used as the method for calculating the blood pressure information. The biological information calculation unit 11 transfers measurement data obtained by associating detection date/time information indicating the date and time of detecting a pulse wave and blood pressure information calculated based on the pulse wave, to the storage control unit 13.

The storage control unit 13 stores the measurement data transferred from the biological information calculation unit 11 in the storage medium 14.

Due to control performed by the storage control unit 13, multiple pieces of measurement data including the blood pressure information calculated by the biological information calculation unit 11 and measurement time information indicating the time of detecting the pulse wave serving as the source of the blood pressure information are stored in the storage medium 14.

The communication unit 16 is an interface for performing communication with an external device through a wire or wirelessly.

The communication control unit 15 performs control for transmitting multiple pieces of measurement data stored in the storage medium 14 to an external device via the communication unit 16.

The diagnosis assistance apparatus 2 includes a communication unit 21, a storage control unit 22, a storage medium 23 such as a flash memory, a ROM, or a memory card, a biological information analysis unit 24, an operation unit 25, an analysis result output unit 26, and a display unit 27.

The storage medium 23 may be detachable from the diagnosis assistance apparatus 2. The storage medium 23 constitutes a storage unit.

The storage control unit 22, the biological information analysis unit 24, and the analysis result output unit 26 are functional blocks that are constituted by a processor executing a diagnosis assistance program.

The diagnosis assistance apparatus 2 may be a dedicated apparatus for diagnosis assistance or may be a general-purpose electronic device such as a smartphone or a tablet terminal.

The communication unit 21 is an interface for performing communication with an external device through a wire or wirelessly.

The display unit 27 displays various types of information for diagnosis assistance, and a display unit using a liquid crystal display element, an organic electroluminescence element, or the like is used thereas.

The display unit 27 need not be built into the diagnosis assistance apparatus 2 and may be provided outside of the diagnosis assistance apparatus 2 and connected through a wire or wirelessly to the diagnosis assistance apparatus 2.

The operation unit 25 is an interface for operating the diagnosis assistance apparatus 2.

The operation unit 25 is constituted by, for example, buttons provided on the diagnosis assistance apparatus 2, a keyboard and a mouse connected to the diagnosis assistance apparatus 2, a touch panel mounted on the display unit 27, or the like.

In a state in which communication between the communication unit 16 of the biological information measurement apparatus 1 and the communication unit 21 has been established, the storage control unit 22 performs a measurement data transmission request to the biological information measurement apparatus 1 via the communication unit 21.

The storage control unit 22 acquires the measurement data received by the communication unit 21 from the biological information measurement apparatus 1 according to the transmission request and stores the received measurement data in the storage medium 23.

The storage control unit 22 compares the measurement data stored in the storage medium 23 and the measurement data stored in the biological information measurement apparatus 1 and performs a request to transmit only new measurement data that has not been stored in the storage medium 23.

The biological information analysis unit 24 analyzes multiple pieces of blood pressure information stored in the storage medium 23 and calculates the occurrence frequency of a fluctuating state (hereinafter referred to also as a "surge") in which the blood pressure information fluctuates by a threshold value or more in a predetermined period, and a representative value for the fluctuation amount (hereinafter referred to also as a "surge fluctuation amount") of the blood pressure information of the surge. The biological information analysis unit 24 stores the calculated surge occurrence frequency and the representative value for the surge fluctuation amount in association with each other in the storage medium 23.

In the present specification, a "state in which the blood pressure information fluctuates by a threshold value or more" refers to a state in which the blood pressure information rises significantly to a certain degree and thereafter drops to near its original value.

As the predetermined period, a period (e.g., a specific day, a specific week, a specific time slot of a specific day) or the like set arbitrarily by a doctor operating the diagnosis assistance apparatus 2 is set through operation of the operation unit 25.

Alternatively, the measurement data stored in the storage medium 23 may be displayed on the display unit 27 as a graph and a period selected through operation of the operation unit 25 in the displayed graph may be set as the predetermined period.

Hereinafter, a blood pressure analysis method performed by the biological information analysis unit 24 will be described with reference to FIGS. 2 and 3.

Figure 2:
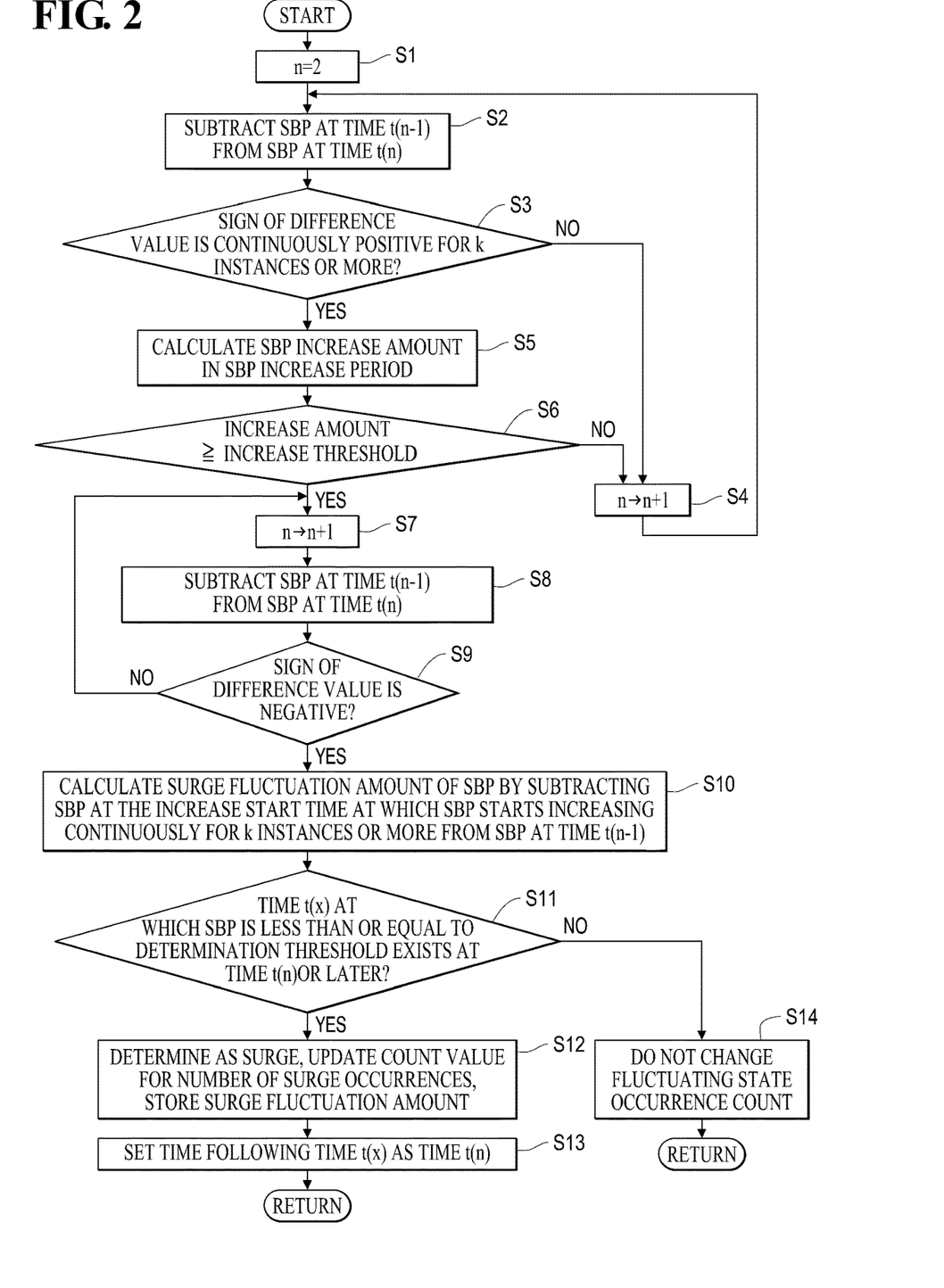
FIG. 2 is a flowchart for describing a blood pressure information analysis method performed by a biological information analysis unit 24.

FIG. 2 is a flowchart for illustrating a blood pressure information analysis method performed by the biological information analysis unit 24.

Figure 3:
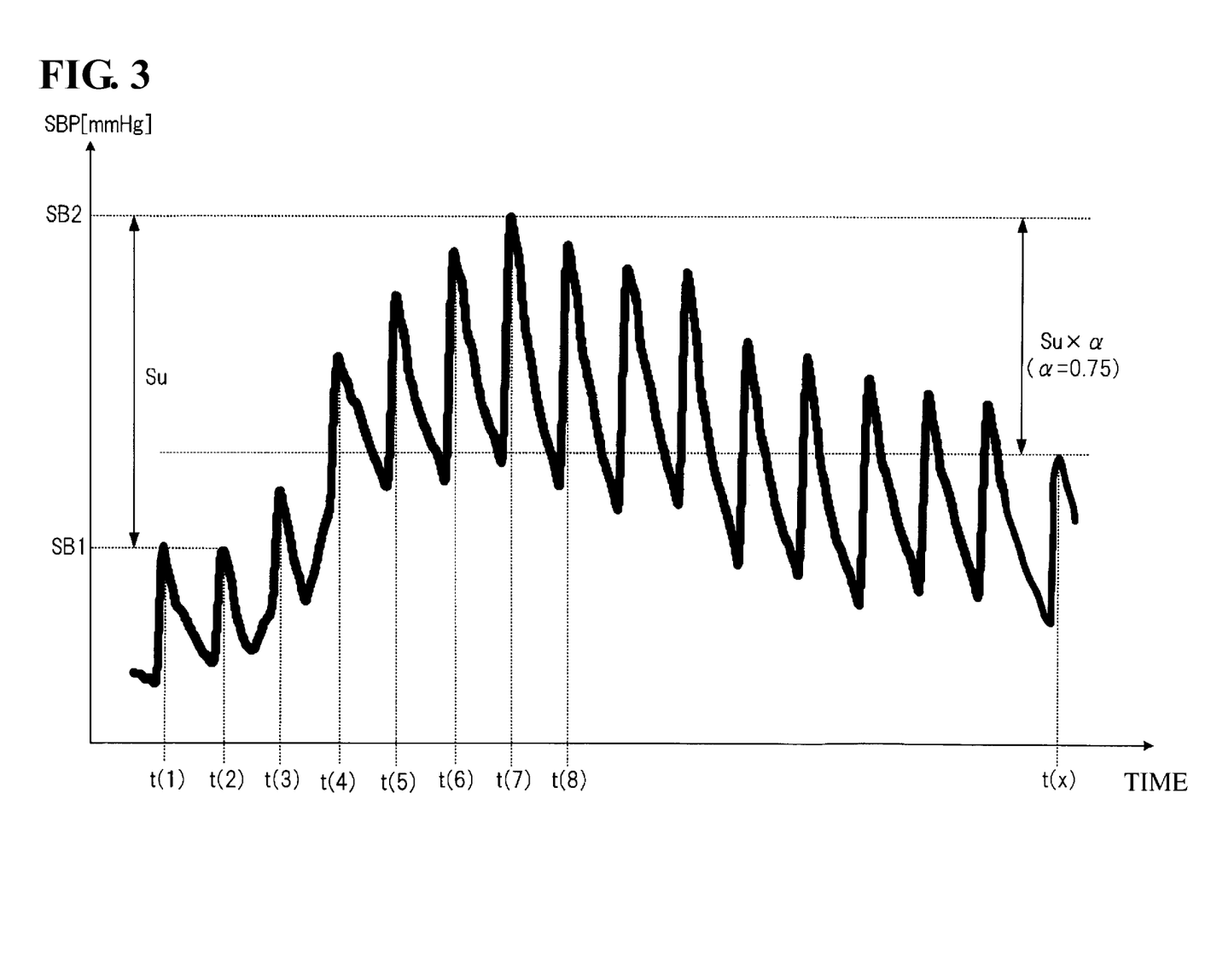
FIG. 3 is a graph showing an example of a portion of a predetermined period's worth of blood pressure information stored in a storage medium 23.

FIG. 3 is a graph showing an example of a portion of a predetermined period's worth of blood pressure information stored in the storage medium 23. The vertical axis of the graph in FIG. 3 indicates SBP, which serves as blood pressure information, and the horizontal axis indicates SBP measurement time (time at which the pulse wave was detected). FIG. 3 shows the SBP over 16 heartbeats.

The biological information analysis unit 24 selects the predetermined period's worth of SBP with the second earliest measurement time, sets the selected measurement time to time t(n), and sets n to an initial value of "2" (step S1).

Next, the biological information analysis unit 24 subtracts the SBP at time t(n−1) from the SBP at time t(n) (step S2). Here, time t(n) means the "n-th" time in the time series, the time being more recent as the number of n is incremented.

The biological information analysis unit 24 determines whether or not the sign of the difference value calculated in step S2 is continuously positive for k (k being any integer greater than or equal to 2) or more instances (step S3). If the result of the determination in step S3 is NO, the biological information analysis unit 24 increases the value of n by 1 (step S4) and returns the processing to step S2.

In the example shown in FIG. 3, when k=3, the sign of the difference value has been continuously positive for 3 instances at the stage at which the difference value has been obtained by subtracting the SBP at time t(4) from the SBP at time t(5). For this reason, at the time point when n=5, the result of the determination in step S3 is YES.

If the result of the determination in step S3 is YES, the biological information analysis unit 24 calculates the increase amount of the SBP in the SBP increase period (step S5).

Specifically, the biological information analysis unit 24 uses the time following the time at which the sign of the difference value calculated in step S2 most recently became negative as the SBP increase start time and calculates the increase amount of the SBP in the SBP increase period by subtracting the SBP at the increase start time from the SBP at time t(n).

In the example shown in FIG. 2, time t(2) is set as the increase start time and the SBP at time t(2) is subtracted from the SBP at time t(5), whereby the increase amount of the SBP in these three SBP increase periods is calculated.

After step S5, the biological information analysis unit 24 determines whether or not the increase amount calculated in step S5 is greater than or equal to a predetermined increase threshold (step S6). If the result of the determination in step S6 is NO, the biological information analysis unit 24 transitions to the processing of step S4.

If the increase amount calculated in step S5 is greater than or equal to the increase threshold (step S6: YES), the biological information analysis unit 24 increases the value of n by 1 (step S7) and performs the processing of step S8, which has the same content as step S2. Note that in the example shown in FIG. 2, it is assumed that the value obtained by subtracting the SBP at time t(2) from the SBP at time t(5) is greater than or equal to the increase threshold.

After step S8, the biological information analysis unit 24 determines whether or not the sign of the difference amount calculated in step S8 is negative (step S9). If the result of the determination in step S9 is NO, the biological information analysis unit 24 returns to the processing of step S7. In the example shown in FIG. 2, the sign of the difference value becomes negative at time t(8), and therefore the result of the determination in step S9 is YES at the time point when n=8.

If the result of the determination in step S9 is YES, the biological information analysis unit 24 calculates the surge fluctuation amount of the SBP by subtracting the SBP at the increase start time of the increase period during which the SBP continuously increases for k instances or more, from the SBP at time t(n−1), which is immediately prior to the time t(n) at which the sign of the difference value became negative (step S10).

In the example shown in FIG. 2, the SBP surge fluctuation amount Su is calculated by the SBP (SB1) at time t(2) being subtracted from the SBP (SB2) at time t(7), which is immediately prior to time t(8) at which the sign of the difference value became negative.

After step S10, the biological information analysis unit 24 calculates, as a determination threshold, a value obtained by multiplying the surge fluctuation amount calculated in step S10 by α (α being a predetermined value that is greater than 0 and less than 1). Then, the biological information analysis unit 24 sequentially compares each of the SBPs at time t(n) and onward with the determination threshold in order starting from the earliest time, and determines whether or not there is a time at which the SBP is less than or equal to the determination threshold (step S11).

If the result of the determination in step S11 is NO, the biological information analysis unit 24 ends the processing without changing the count value for the number of surge occurrence instances.

If the biological information analysis unit 24 determines that there is a time (t(x)) at which the SBP is less than or equal to the determination threshold (step S11: YES), the biological information analysis unit 24 determines that a surge occurred, increases the count value for the number of surge occurrence instances (the initial value of which is zero) by 1, and stores the surge fluctuation amount calculated in step S10 in the storage medium 23 (step S12).

In the example shown in FIG. 2, the SBP is less than or equal to a times the surge fluctuation amount Su at time t(x), and therefore at this time point, the surge fluctuation amount Su is stored in the storage medium 23 and the count value for the number of surge occurrence instances is increased by 1.

After step S12, the biological information analysis unit 24 sets the time following time t(x) as time t(n) (step S13) and repeats the processing of step S1 and onward.

Note that in the processing of step S13, the biological information analysis unit 24 ends the processing if time t(n) reaches the final time of the predetermined period or if time t(n) is a time outside of the predetermined period. Also, in the processing of step S4, the biological information analysis unit 24 ends the processing also if time t(n) reaches the final time of the predetermined period.

As described above, if the state in which the SBP increases continues for multiple instances and the increase amount of the SBP during the multiple instances of SBP increase is greater than or equal to an increase threshold, and furthermore, if the reduction of the SBP by a value obtained by multiplying a coefficient α by the difference (surge fluctuation amount SU in FIG. 2) between the SBP at the time (time t(7) in FIG. 2) immediately prior to the time (time t(8) in FIG. 2) at which the SBP started to decrease after the multiple instances of SBP increase and the SBP at the start time (time t(2) in FIG. 2) of the multiple instances of SBP increase was after the above-described immediately-prior time, the biological information analysis unit 24 determines this as a fluctuating state (surge) in which the SBP fluctuated by a threshold value or more, calculates the above-described difference as the SBP fluctuation amount in the fluctuating state, and stores the calculated SBP fluctuation amount.

The analysis method shown in FIG. 2 is effective for acquiring the fluctuation of the blood pressure information that occurs when a patient with sleep apnea syndrome enters an apneic state.

The biological information analysis unit 24 calculates the surge occurrence frequency in the above-described predetermined period based on the count value after the end of the processing shown in FIG. 3, and stores the information on the occurrence frequency in the storage medium 23.

Regarding the occurrence frequency, there is a method in which the count value itself is stored in the storage medium 23 as the information on the occurrence frequency, a method in which the number of occurrences of the fluctuating state per predetermined unit time is obtained based on the count value and the predetermined period, and the number of occurrences per unit time is stored in the storage medium 23 as the information on the occurrence frequency, and the like.

For example, if the predetermined period is 10 minutes, the count value in the predetermined period is 14, and the unit time is one hour, then the biological information analysis unit 24 performs processing for converting the count value for 10 minutes into a count value for one hour by multiplying by 6, and thus generates 84 [times/hour] as the information on the occurrence frequency.

Alternatively, for example, if the predetermined period is 5 hours, the count value for 5 hours is 120, and the unit time is 1 hour, the biological information analysis unit 24 performs processing for converting the count value for 5 hours into a count value for 1 hour by dividing by 5, and thus generates 24 [times/hour] as the information on the occurrence frequency.

The biological information analysis unit 24 calculates a representative value for the surge fluctuation amount in the predetermined period based on the surge fluctuation amount in the above-described predetermined period stored in the storage medium 23, and stores the calculated representative value in the storage medium 23 in association with the above-described information on the occurrence frequency.

The biological information analysis unit 24 analyzes the blood pressure information in the predetermined period and stores the surge fluctuation amount with the largest value among the stored surge fluctuation amounts as the representative value in the storage medium 23, analyzes the blood pressure information in the predetermined period and stores the average value of all of the stored surge fluctuation amounts as the representative value in the storage medium 23, or analyzes the blood pressure information in the predetermined period and stores the mode of the stored surge fluctuation amounts as the representative value in the storage medium 23. The representative value need only be a value according to which it is possible to determine the trend of the surge fluctuation amounts in the predetermined period, and there is no limitation on these values.

The analysis result output unit 26 generates image information indicating the information on the surge occurrence frequency and the representative value of the surge fluctuation amount, which are the results of analyzing the blood pressure information stored in association with each other in the storage medium 23, and outputs the generated image information to the display unit 27. The display unit 27 displays an image based on the image information output from the analysis result output unit 26.

The image information need only be image information according to which the correlational relationship between the surge occurrence frequency and the representative value for the surge fluctuation amount can be easily determined visually. Specifically, as the image information, the analysis result output unit 26 generates a graph indicating the correlational relationship between the occurrence frequency and the representative value stored in the storage medium 23, with the surge occurrence frequency on a first axis and the representative value for the surge fluctuation amount on a second axis.

Figure 4:
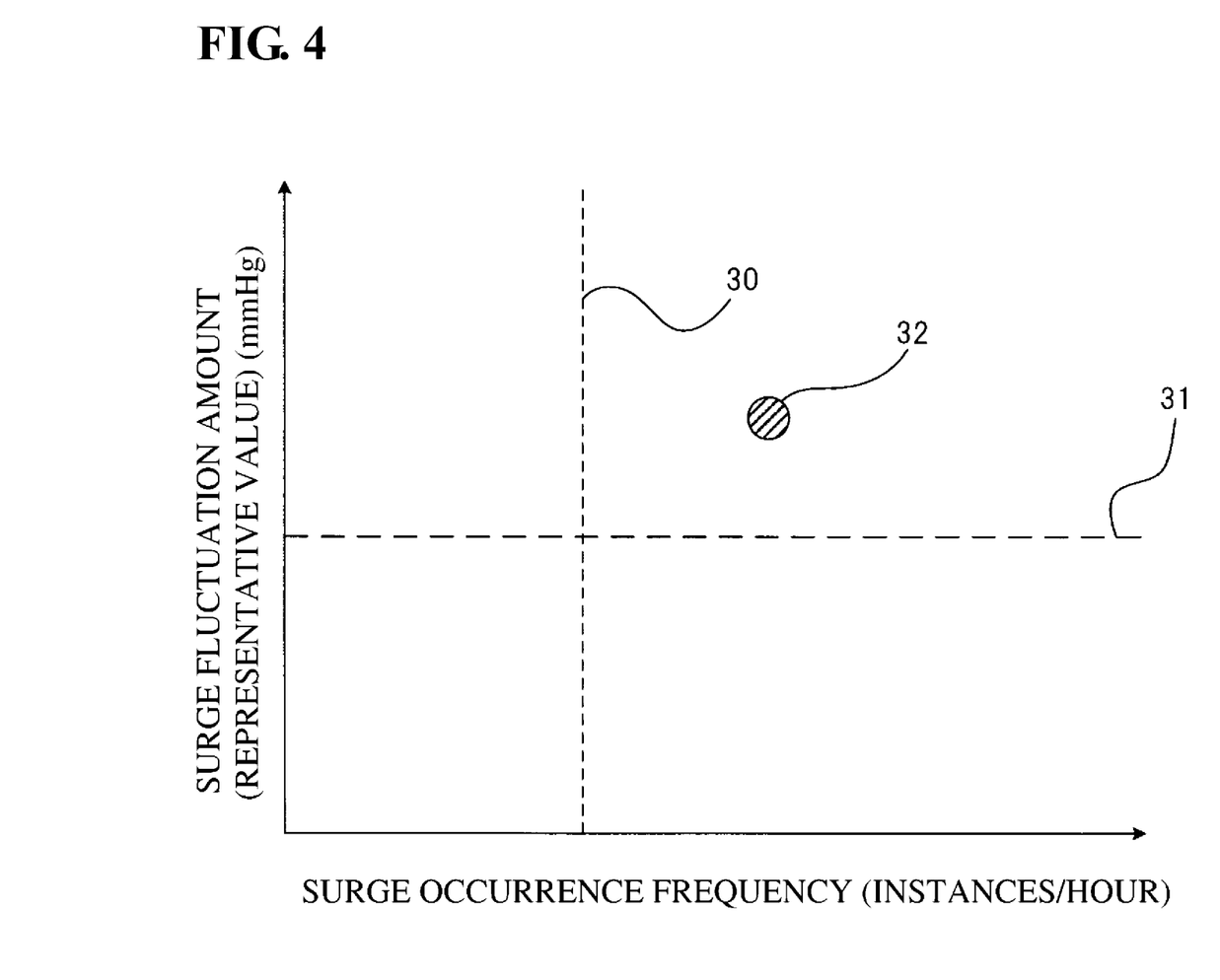
FIG. 4 is a diagram showing an example of a graph generated by an analysis result output unit 26.

FIG. 4 is a diagram showing an example of a graph generated by the analysis result output unit 26.

In the graph shown in FIG. 4, the horizontal axis, which is the first axis, indicates the surge occurrence frequency, and the vertical axis, which is the second axis, indicates the representative value for the surge fluctuation amount. In FIG. 4, the vertical axis may indicate the surge occurrence frequency and the horizontal axis may indicate the representative value for the surge fluctuation amount.

A correspondence point 32 at which the occurrence frequency and the representative value that were generated by the biological information analysis unit 24 and stored in the storage medium 23 intersect is plotted on the graph shown in FIG. 4. Also, the graph shown in FIG. 4 includes a first straight line 31 that is parallel to the horizontal axis and at which the value on the vertical axis takes a predetermined value, and a second straight line 30 that is parallel to the vertical axis and at which the value on the horizontal axis takes a predetermined value.

According to the graph shown in FIG. 4, regarding the blood pressure information of the measurement subject, the relationship between the surge occurrence frequency and the fluctuation amount of the blood pressure information when the surge occurs can be understood instantaneously. It is effective to comprehensively determine the risk of a cardiovascular event such as a cardiac infarction or a cerebral infarction based on the information on both the surge occurrence frequency and the fluctuation amount of the blood pressure information when a surge occurs, instead of the information on only one of the above.

For this reason, as shown in FIG. 4, by presenting the graph including the correspondence point 32 indicating the surge occurrence frequency and the representative value for the surge fluctuation amount to the doctor, it is possible to assist determination of a treatment plan for the measurement subject.

Also, as shown in FIG. 4, by displaying the first straight line 31 and the second straight line 30 on the graph, four types of the measurement subject are established using the four quadrants divided by the first straight line 31 and the second straight line 30, and thus it is possible to instantaneously understand what type the measurement subject is.

The position on the vertical axis of the first straight line 31 and the position on the horizontal axis of the second straight line 30 are preferably set to values determined in advance through the experience of the doctor or the like, but the positions may be set manually to any values by operating the operation unit 25. By doing so, the doctor can use his or her own experience or the like to set the values, making it easier to determine a treatment plan.

Also, the types of measurement subject can be further subdivided by displaying multiple straight lines with different positions on the vertical axis as first straight lines 31 on the graph, displaying multiple straight lines with different positions on the horizontal axis as second straight lines 30 on the graph, or displaying multiple first straight lines 31 and multiple second straight lines 30 on the graph.

Figure 5:
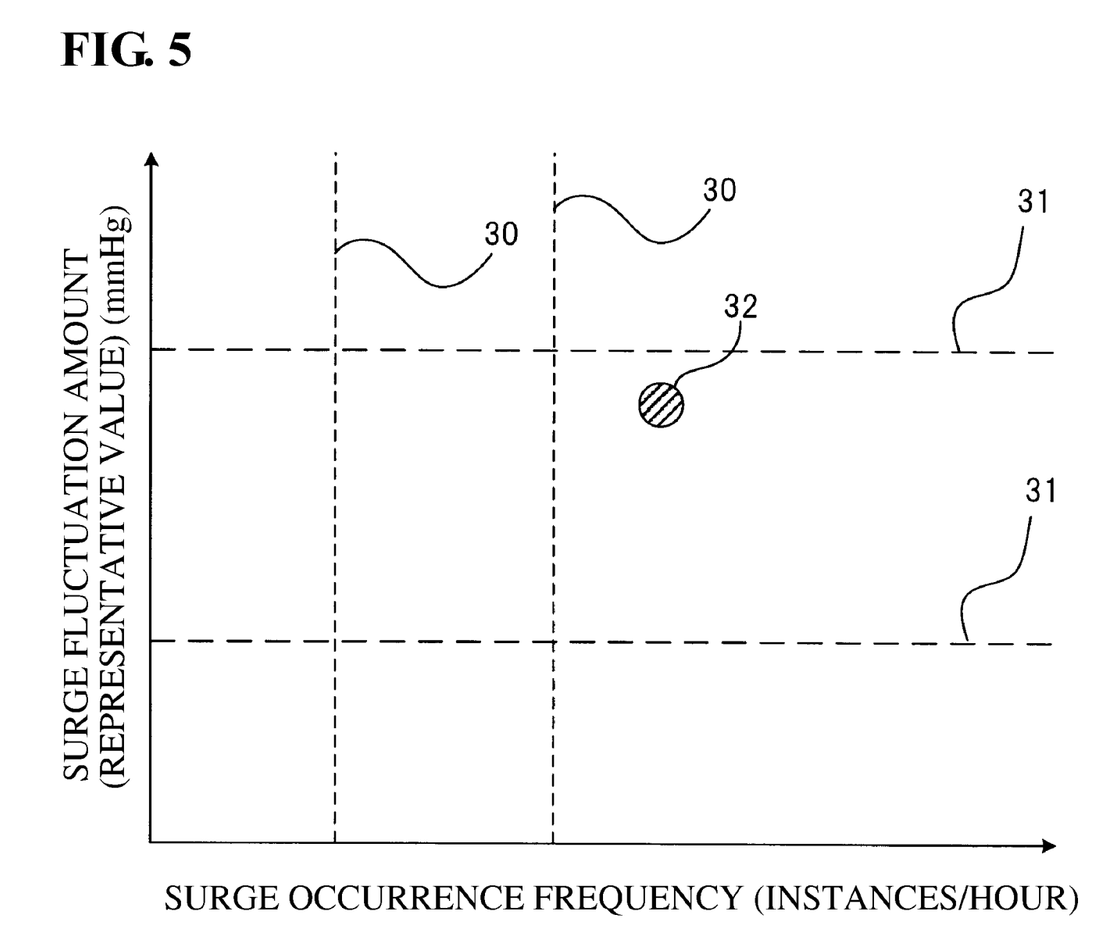
FIG. 5 is a diagram showing another example of a graph generated by the analysis result output unit 26.

FIG. 5, is a diagram showing an example in which two first straight lines 31 and two second straight lines 30 are displayed on the graph. By doing so, the doctor can more easily determine a treatment plan and effective diagnosis assistance is possible.

The number of first straight lines 31 and the number of second straight lines 30 may also be set manually to any number by operating the operation unit 25. By doing so, the doctor can more easily determine a treatment plan and effective diagnosis assistance is possible.

As described above, according to the diagnosis assistance apparatus 2, it is possible to instantaneously understand the relationship between the occurrence frequency of surges in which the blood pressure information of the measurement subject fluctuates significantly and the surge fluctuation amount using the graph illustrated in FIG. 4, which is displayed on the display unit 27. This graph serves as a determination material for determining which treatment the measurement subject needs, and therefore can be useful in diagnosis performed by a doctor.

With the diagnosis assistance apparatus 2, the image information is presented to the doctor by displaying an image based on the image information output from the analysis result output unit 26 on the display unit 27. As a modified example of this, a printer may be used instead of the display unit 27, and the image based on the image information output from the analysis result output unit 26 may be printed onto paper by the printer.

Also, with the diagnosis assistance apparatus 2, blood pressure information is treated as the biological information, but the biological information that can be handled by the diagnosis assistance apparatus 2 need only be biological information that indicates circulatory dynamics in which sudden fluctuation can occur. For example, the biological information may be the heart rate, pulse rate, or the like.

Also, with the diagnosis assistance apparatus 2, a graph (image information) indicating the relationship between the surge occurrence frequency and the representative value for the surge fluctuation amount is displayed or printed by the display unit 27 or a printer, but the content that is displayed or printed need not be image information.

For example, a configuration is also possible in which the surge occurrence frequency and the representative value for the surge fluctuation amount are displayed or printed as simple numeric values. With this kind of configuration as well, it is possible to determine the type of the measurement subject and effective diagnosis assistance is achieved.

The first straight line 31 illustrated in FIG. 4 need only be at least a portion of a straight line at which the value on the vertical axis is a constant value on the graph. For example, as with the graph illustrated in FIG. 6, the left end of the first straight line 31 need not intersect with the vertical axis.

Similarly, the second straight line 30 illustrated in FIG. 4 need only be at least a portion of a straight line at which the value on the horizontal axis is a constant value on the graph. For example, as with the graph illustrated in FIG. 6, the lower end of the second straight line 30 need not intersect with the horizontal axis. Note that the first straight line and the second straight line need to intersect with each other.

In the description above, an example was shown in which the surge fluctuation amount (the amount of change from when the blood pressure information started to rise to when the blood pressure information reached its peak) is used as the information on the vertical axis of the graph shown in FIG. 4. However, the information on the vertical axis of the graph shown in FIG. 4 need only be information indicating the fluctuation content of the blood pressure information when a fluctuating state occurs. The surge fluctuation amount is one piece of information indicating the fluctuation content of the blood pressure information.

An integrated value (hereinafter referred to as "surge area") of the blood pressure information in the period (e.g., the period from time $t(2)$ to time $t(x)$ in FIG. 3) in which the fluctuating state occurred may also be used as the information indicating the fluctuation content of the blood pressure information. According to this integrated value, it is possible to obtain the amount of time from when the blood pressure fluctuation occurred to when the blood pressure returned to its original state (degree to which the blood pressure returns to normal). For this reason, the integrated value is effective as the information on the vertical axis in FIG. 4.

Also, the peak value (the value at time $t(7)$ in FIG. 3; hereinafter referred to as "surge peak value") of the blood pressure information in the period in which the fluctuating state occurred may be used as information indicating the fluctuation content of the blood pressure information. According to this surge peak value, the degree of the surge can be obtained. For this reason, the integrated value is effective as the information on the vertical axis in FIG. 4.

Also, the fluctuation speed of the blood pressure information in the period in which the fluctuating state occurred may be used as information indicating the fluctuation content of the blood pressure information. In the example shown in FIG. 3, the amount of time from time $t(2)$ at which the fluctuating state occurred to time $t(7)$ at which the SBP reached its peak may be used as the information indicating the fluctuation speed of the blood pressure information.

Also, in the example shown in FIG. 3, a value (hereinafter referred to as "rising surge speed") obtained by dividing the surge fluctuation amount Su by the amount of time from time $t(2)$ at which the fluctuating state occurred to time $t(7)$ at which the SBP reached its peak may be used as the information indicating the fluctuation speed of the blood pressure information.

Also, in the example shown in FIG. 3, a value (hereinafter referred to as "falling surge speed") obtained by dividing the surge fluctuation amount Su by the amount of time from time $t(7)$ at which the SBP reached its peak to time $t(x)$ at which the fluctuating state ended may be used as the information indicating the fluctuation speed of the blood pressure information.

According to these pieces of information indicating the fluctuation speed, it is possible to understand how suddenly the blood pressure fluctuation occurred. For this reason, these pieces of information are effective as the information on the vertical axis in FIG. 4.

Also, the length of the period (hereinafter referred to as "surge time") in which the fluctuating state occurred may be used as information indicating the fluctuation content of the blood pressure information. In the example shown in FIG. 3, the amount of time from time t(2) at which the fluctuating state occurred to time t(x) at which the fluctuating state ended is the surge time.

The biological information analysis unit 24 preferably stores representative values for at least two pieces of information selected from the surge fluctuation amount, the surge area, the surge peak value, the rising surge speed, the falling surge speed, and the surge time, in association with the information on the above-described occurrence frequency in the storage medium 23.

In this case, the analysis result output unit 26 generates information indicating the analysis result associated with the multiple representative values and the information on the surge occurrence frequency, which were stored in association with each other in the storage medium 23, and outputs the generated information to the display unit 27.

For example, the analysis result output unit 26 generates at least two of the following six graphs and outputs them to the display unit 27.

(1) A first graph in which the surge occurrence frequency is indicated on the first axis and the representative value for the surge fluctuation amount is indicated on the second axis.

(2) A second graph in which the surge occurrence frequency is indicated on the first axis and the representative value for the surge area is indicated on the second axis.

(3) A third graph in which the surge occurrence frequency is indicated on the first axis and the representative value for the surge peak value is indicated on the second axis.

(4) A fourth graph in which the surge occurrence frequency is indicated on the first axis and the representative value for the rising surge speed is indicated on the second axis.

(5) A fifth graph in which the surge occurrence frequency is indicated on the first axis and the representative value for the falling surge speed is indicated on the second axis.

(6) A sixth graph in which the surge occurrence frequency is indicated on the first axis and the representative value for the surge time is indicated on the second axis.

Accordingly, due to multiple graphs with different representative values on the second axis being displayed on the display unit 27, the amount of the information needed for diagnosis increases. For this reason, the doctor can more easily determine a treatment plan and effective diagnosis assistance is possible.

Figure 6:
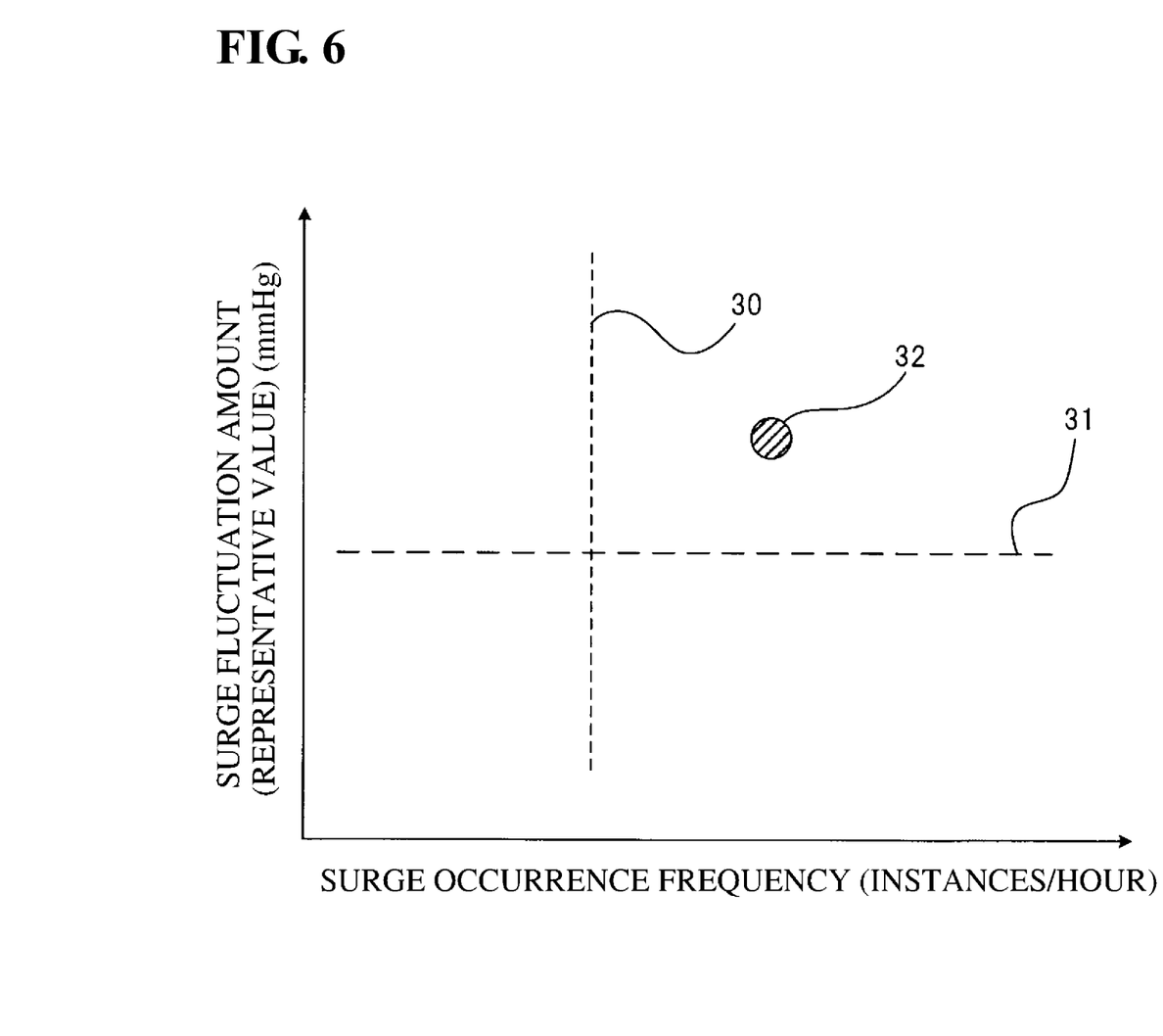
FIG. 6 is a diagram showing yet another example of a graph generated by the analysis result output unit 26.

Note that as illustrated in FIGS. 4 to 6, with a graph including at least one first straight line 31 and at least one second straight line 30, it is possible to determine that among the at least four quadrants divided by the straight lines, the further upward and to the right the quadrant in which the correspondence point 32, which is the intersection between the numerical values on the vertical axis and the horizontal axis, is plotted is, the higher the risk of disease is.

In view of this, the analysis result output unit 26 preferably generates multiple graphs indicating analysis results and selects and outputs the graph in which it is determined that the risk is the highest (the graph with the greatest distance between the intersection of the horizontal axis and the vertical axis and the quadrant in which the correspondence portion 32 is plotted) among the multiple graphs. Accordingly, since only the graph in which it can be determined that the risk is the highest is displayed on the display unit 27, it is possible to assist efficient diagnosis.

In the above description, the biological information analysis unit 24 determines the state in which the blood pressure information increases and then decreases as a fluctuating state of the blood pressure information and calculates the surge occurrence frequency. There is no limitation to this, and the biological information analysis unit 24 may determine a state in which the blood pressure information decreases and then increases as a fluctuating state of the blood pressure and calculate the blood pressure drop occurrence frequency. In this case as well, by generating and outputting information indicating the correspondence between the blood pressure drop occurrence frequency and the representative value for the blood pressure drop amount (information indicating the blood pressure drop content), it is possible to contribute to diagnosis.

The embodiments disclosed herein are to be considered in all respects exemplary and not limiting. The scope of the present invention is indicated by the claims and not the above description, and is intended to encompass all modifications within the meaning and range equivalent to the claims.

The diagnosis assistance program of the present embodiment is stored in a computer-readable non-transitory storage medium. Such a "computer-readable storage medium" includes, for example, optical media such as CD-ROMs (compact disc-ROMs), magnetic storage media such as memory cards, and the like. Also, this program can be provided through downloading via a network.

As described above, the following items are disclosed in the present specification.

The disclosed diagnosis assistance apparatus includes: a biological information analysis unit configured to analyze a plurality of pieces of biological information that are measured from a measurement subject and are stored along with measurement times in a storage unit, and calculate an occurrence frequency of a fluctuating state in which the biological information fluctuates by a threshold or more in a predetermined period and a representative value for information indicating fluctuation content of the biological information in the fluctuating state that occurs in the predetermined period; and an analysis result output unit configured to output information indicating an analysis result obtained by associating the occurrence frequency and the representative value that were calculated by the biological information analysis unit.

With the disclosed diagnosis assistance apparatus, the analysis result output unit outputs, as the information, a graph indicating a relationship between the occurrence frequency and the representative value, which were calculated by the biological information analysis unit, with the occurrence frequency of the fluctuating state indicated on a first axis and the representative value for the information indicating the fluctuation content of the biological information indicated on a second axis.

With the disclosed diagnosis assistance apparatus, as the graph, the analysis result output unit outputs, as the information, a graph including at least one first straight line at which a value on the first axis takes a predetermined value, and at least one second straight line at which a value on the second axis takes a predetermined value, the second straight line intersecting with the first straight line.

With the disclosed diagnosis assistance apparatus, the value on the first axis of the first straight line and the value on the second axis of the second straight line may be set manually.

With the disclosed diagnosis assistance apparatus, the number of the first straight lines and the number of the second straight lines may be set manually.

With the disclosed diagnosis assistance apparatus, if a state in which the biological information increases continues for a plurality of instances and an increase amount of the biological information during the plurality of instances in which the biological information increases is greater than or equal to an increase threshold, and furthermore, if a decrease in the biological information by a value obtained by multiplying a coefficient that is greater than 0 and less than 1 by a difference between the biological information at a time immediately prior to a time at which the biological information starts to decrease after the plurality of instances in which the biological information increases and the biological information at a start time of the plurality of instances in which the biological information increases occurs after the immediately-prior time, the biological information analysis unit determines that the biological information is in a fluctuating state of fluctuating by a threshold or more.

With the disclosed diagnosis assistance apparatus, the information indicating the fluctuation content of the biological information in the fluctuating state may be at least one selected from a fluctuation amount of the biological information in a period in which the fluctuating state occurs, an integrated value of the biological information in the period in which the fluctuating state occurs, a peak value of the biological information in the period in which the fluctuating state occurs, a fluctuation speed of the biological information in the period in which the fluctuating state occurs, and a length of the period in which the fluctuating state occurs.

With the disclosed diagnosis assistance apparatus, the biological information may be blood pressure information.

The disclosed diagnosis assistance method includes a biological information analysis step of analyzing a plurality of pieces of biological information that are measured from a measurement subject and are stored along with measurement times in a storage unit, and calculating an occurrence frequency of a fluctuating state in which the biological information fluctuates by a threshold or more in a predetermined period and a representative value for information indicating fluctuation content of the biological information in the fluctuating state that occurs in the predetermined period; and an analysis result output step of outputting information indicating an analysis result obtained by associating the occurrence frequency and the representative value that were calculated in the biological information analysis step.

The disclosed diagnosis assistance program is for causing a computer to execute a biological information analysis step of analyzing a plurality of pieces of biological information that are measured from a measurement subject and are stored along with measurement times in a storage unit, and calculating an occurrence frequency of a fluctuating state in which the biological information fluctuates by a threshold or more in a predetermined period and a representative value for information indicating fluctuation content of the biological information in the fluctuating state that occurs in the predetermined period; and an analysis result output step of outputting information indicating an analysis result obtained by associating the occurrence frequency and the representative value that were calculated in the biological information analysis step.

INDUSTRIAL APPLICABILITY

The present invention can effectively assist diagnosis by making it possible to easily understand the state of the biological information of the measurement subject, and therefore can be used in a medical institution.

Although the present invention has been described above by means of specific embodiments, the present invention is not limited to the embodiments, and various modifications are possible without departing from the technical gist of the disclosed invention. The present application is based on Japanese Patent Application 2015-220588 filed on Nov. 10, 2015, the content of which is incorporated herein in its entirety.

REFERENCE SIGNS LIST

1 Biological information measurement apparatus
2 Diagnosis assistance apparatus
23 Storage medium (storage unit)
24 Biological information analysis unit
26 Analysis result output unit
Su Surge fluctuation amount
31 First straight line
30 Second straight line
32 Correspondence point

The invention claimed is:

1. A diagnosis assistance apparatus comprising:
a processor programmed to:
analyze a plurality of pieces of biological information that are measured from a measurement subject and that are stored together with measurement times in a memory;
determine that the biological information is in a fluctuating state of fluctuating by a threshold or more in a predetermined period if the biological information increases by an increase threshold or more and thereafter decreases by a determination threshold in the predetermined period;
calculate an occurrence frequency of a-the fluctuating state;
calculate a representative value for information indicating fluctuation content of the biological information in the fluctuating state that occurs in the predetermined period, the fluctuation content being at least one of: (i) a fluctuation amount of the biological information, (ii) an integrated value of the biological information, (iii) a peak value of the biological information, (iv) a fluctuation speed of the biological information, and/or (v) a length of the period in which the fluctuating state occurs; and
output a graph indicating a relationship between the calculated occurrence frequency and the calculated representative value with the calculated occurrence frequency of the fluctuating state being indicated on a first axis and the calculated representative value for the information indicating the fluctuation content of the biological information being indicated on a second axis.

2. The diagnosis assistance apparatus according to claim 1, wherein
the graph includes: (a) at least one first straight line at which a value on the first axis takes a predetermined value, and (b) at least one second straight line at which a value on the second axis takes a predetermined value, the second straight line intersecting with the first straight line.

3. The diagnosis assistance apparatus according to claim 2, wherein the value on the first axis of the first straight line and the value on the second axis of the second straight line is set manually.

4. The diagnosis assistance apparatus according to claim 2, wherein the number of the first straight lines and the number of the second straight lines is set manually.

5. The diagnosis assistance apparatus according to claim 1, wherein
the biological information analysis unit determines that the biological information is in a fluctuating state of fluctuating by a threshold or more if:
a state in which the biological information increases continues for a plurality of instances and an increase amount of the biological information during the plurality of instances in which the biological information increases is greater than or equal to an increase threshold, and
a value obtained by multiplying a coefficient that is greater than 0 and less than 1 by a difference between the biological information at a time immediately prior to a time at which the biological information starts to decrease after the plurality of instances in which the biological information increases and the biological information at a start time of the plurality of instances in which the biological information increases is calculated as the determination threshold and a decrease in the biological information by the determination threshold occurs after the immediately-prior time.

6. The diagnosis assistance apparatus according to claim 1, wherein the biological information is blood pressure information.

7. A diagnosis assistance method comprising:
analyzing a plurality of pieces of biological information that are measured from a measurement subject and are stored together with measurement times in a memory;
determining that the biological information is in a fluctuating state of fluctuating by a threshold or more in a predetermined period if the biological information increases by an increase threshold or more and thereafter decreases by a determination threshold in the predetermined period;
calculating an occurrence frequency of the fluctuating state;
calculating a representative value for information indicating fluctuation content of the biological information in the fluctuating state that occurs in the predetermined period, the fluctuation content being at least one of: (i) a fluctuation amount of the biological information, (ii) an integrated value of the biological information, (iii) a peak value of the biological information, (iv) a fluctuation speed of the biological information, and/or (v) a length of the period in which the fluctuating state occurs; and
outputting a graph indicating a relationship between the calculated occurrence frequency and the calculated representative value with the calculated occurrence frequency of the fluctuating state being indicated on a first axis and the calculated representative value for the information indicating the fluctuation content of the biological information being indicated on a second axis.

8. A non-transitory computer readable medium storing a diagnosis assistance program that causes a computer to execute steps comprising:
analyzing a plurality of pieces of biological information that are measured from a measurement subject and that are stored together with measurement times in a memory;
determining that the biological information is in a fluctuating state of fluctuating by a threshold or more in a predetermined period if the biological information increases by an increase threshold or more and thereafter decreases by a determination threshold in the predetermined period;
calculating an occurrence frequency of the fluctuating state;
calculating a representative value for information indicating fluctuation content of the biological information in the fluctuating state that occurs in the predetermined period, the fluctuation content being at least one of: (i) a fluctuation amount of the biological information, (ii) an integrated value of the biological information, (iii) a peak value of the biological information, (iv) a fluctuation speed of the biological information, and/or (v) a length of the period in which the fluctuating state occurs; and
outputting a graph indicating a relationship between the calculated occurrence frequency and the calculated representative value with the calculated occurrence frequency of the fluctuating state being indicated on a first axis and the calculated representative value for the information indicating the fluctuation content of the biological information being indicated on a second axis.

\* \* \* \* \*